(12) United States Patent
Kim et al.

(10) Patent No.: US 11,576,989 B2
(45) Date of Patent: Feb. 14, 2023

(54) APPARATUS FOR TREATING SURFACE OF MEDICAL METAL

(71) Applicant: DIO CORPORATION, Busan (KR)

(72) Inventors: Jin Chui Kim, Busan (KR); Jin Baek Kim, Busan (KR)

(73) Assignee: DIO CORPORATION, Busan (KR)

( * ) Notice: Subject to any disclaimer, the term of this patent is extended or adjusted under 35 U.S.C. 154(b) by 285 days.

(21) Appl. No.: 16/753,903

(22) PCT Filed: Apr. 11, 2019

(86) PCT No.: PCT/KR2019/004342
§ 371 (c)(1),
(2) Date: Apr. 6, 2020

(87) PCT Pub. No.: WO2020/204244
PCT Pub. Date: Oct. 8, 2020

(65) Prior Publication Data
US 2021/0268133 A1 Sep. 2, 2021

(30) Foreign Application Priority Data

Mar. 29, 2019 (KR) .................. 10-2019-0036830

(51) Int. Cl.
*A61L 2/10* (2006.01)
*A61L 27/04* (2006.01)

(52) U.S. Cl.
CPC .............. *A61L 2/10* (2013.01); *A61L 27/04* (2013.01); *A61L 2202/11* (2013.01); *A61L 2202/122* (2013.01); *A61L 2202/13* (2013.01); *A61L 2202/14* (2013.01); *A61L 2202/17* (2013.01); *A61L 2202/21* (2013.01); *A61L 2430/12* (2013.01)

(58) Field of Classification Search
None
See application file for complete search history.

(56) References Cited

U.S. PATENT DOCUMENTS

2017/0368215 A1* 12/2017 Shatalov ................ H04N 5/332

FOREIGN PATENT DOCUMENTS

| CN | 204814948 U | 12/2015 |
| CN | 109174782 A | 1/2019 |

(Continued)

OTHER PUBLICATIONS

Office Action issued to Indian Patent Application 202027013200 dated Nov. 10, 2021, 5 pages.

(Continued)

*Primary Examiner* — Andrew Smyth
(74) *Attorney, Agent, or Firm* — K&L Gates LLP (57) ABSTRACT

Provided is an apparatus for treating a surface of a medical metal. The apparatus includes a lamp unit in which a through-hole is formed and which irradiates the through-hole with ultraviolet rays, a lifting unit on which a container accommodating a medical metal is detachably disposed and which is disposed to be movable in the through-hole, and a case unit which accommodates the lamp unit and the lifting unit and includes an outer case in which an outer hole corresponding to the through-hole is formed and an inner case which is disposed inside the outer case and in which the lamp unit or the lifting unit is disposed.

12 Claims, 5 Drawing Sheets

FIG. 4

(56) References Cited

FOREIGN PATENT DOCUMENTS

| | | |
|---|---|---|
| JP | 2005-211649 | 8/2005 |
| JP | 2021157412 | 8/2012 |
| JP | 2016-137054 | 8/2016 |
| JP | 6048915 B2 | 12/2016 |
| KR | 1020110131551 A | 7/2011 |
| KR | 1020160049683 A | 5/2016 |
| KR | 10-1769783 | 8/2017 |
| KR | 101889973 B1 | 11/2017 |
| KR | 1020180092648 A | 8/2018 |
| KR | 101904017 B1 | 10/2018 |
| KR | 10-2019-0088759 | 7/2019 |
| TW | 201800113 | 1/2018 |
| WO | 2012-105094 | 8/2012 |
| WO | 2017191925 | 11/2017 |
| WO | WO-2019216485 A1 * | 11/2019 ............. A61C 19/06 |

OTHER PUBLICATIONS

Extended European Search Report issued to EP Patent Application 19922793.5 dated Nov. 26, 2021, 9 pages.

* cited by examiner

APPARATUS FOR TREATING SURFACE OF MEDICAL METAL

CROSS-REFERENCE TO RELATED APPLICATIONS

This application is the National Stage filing under 35 U.S.C. 371 of International Application No. PCT/KR2019/004342 filed on Apr. 11, 2019, which claims the benefit of earlier filing date and right of priority to Korean Application No. 10-2019-0036830 filed on Mar. 29, 2019, the contents of which are all hereby incorporated by reference herein in their entirety.

TECHNICAL FIELD

The present invention relates to an apparatus for treating a surface of a medical metal, and more particularly, to an apparatus for treating a surface of a medical metal, which is for maintaining or modifying a surface of a fixture of a dental implant to be a hydrophilic surface.

BACKGROUND ART

Medical metals that can be implanted into a human body should not only be made of highly stable biocompatible materials for human biological tissues but should also have no chemical or physiological reactivity or be not rejected by a human body.

For example, as a representative use of the medical metal, there is a fixture used for dental implants. Although there have been attempts to develop various metals or alloys as materials appropriate for such a fixture, currently, titanium metals or titanium alloys are mainly in use.

However, the titanium or titanium alloy itself takes a long time to fuse to the bone when being transplanted in the human body, and an oxide film is generated thereon and thus stability is ensured as compared to other metals, but recently, there is a need for more improved stability for human safety.

Therefore, techniques in which bone fusion can be improved by appropriately treating a surface of a medical metal are being developed and applied.

Specifically, quality associated with a rate of bone fusion is closely related to properties and chemical composition of the surface of the metal, such as surface composition, a surface roughness, hydrophilicity, and the like. In particular, metals having a highly hydrophilic surface are known to be advantageous for interaction with biological solutions, cells, and tissues.

However, the surface of the medical metal is stabilized by carbon atoms being bonded thereto as time has elapsed after oxide film treatment, and thus the surface of the medical metal is changed to a hydrophobic surface in a low energy state. As a result, when a fixture made of such a medical metal is implanted in an alveolar bone without change, bone fusion performance is reduced, and when a surface of the fixture is contaminated by organic matter, inflammation may be caused in a state in which the fixture is implanted.

In order to address the above problem, recently, an ultraviolet ray irradiation apparatus for surface treatment is being developed in which a fixture is mounted therein and then ultraviolet rays are applied to the fixture, and thus a surface of the fixture may be modified and organic contaminants attached to the surface may be removed.

In Korean Laid-open Patent Application No. 10-2018-0092648 (Title: ULTRAVIOLET RAY IRRADIATION APPARATUS FOR IMPLANT), the conventional surface treatment apparatus is disclosed in which an implant container accommodating a fixture is disposed between a plurality of ultraviolet ray lamps so that surface modification is performed.

However, such a conventional apparatus has a problem in that rapid implant progress cannot be performed because the ultraviolet rays applied for the surface modification of the fixture are not uniformly applied on the entire surface, and thus there is a need for the fixture to be exposed to the ultraviolet rays for a long time for the surface modification of the entire fixture.

In addition, such a conventional apparatus has a problem in that because the ultraviolet rays are applied to the fixture for a long time, it takes more time to cool the heated fixture, and thus a rapid implant progress cannot be performed.

Further, the ultraviolet rays may be generated in a low temperature plasma method. Since such a plasma method involves the generation of ozone, there is a problem in that the conventional apparatus for modifying the surface of the medical metal should be used in an extremely limited space.

DISCLOSURE

Technical Problem

The present invention is directed to providing an apparatus for treating a surface of a medical metal, in which modification of the surface of the medical metal may be effectively performed and ozone generated from a lamp may be effectively removed, thereby ensuring safety of use.

Technical Solution

One aspect of the present invention provides an apparatus for treating a surface of a medical metal, which includes a lamp unit in which a through-hole is formed and which irradiates the through-hole with ultraviolet rays, a lifting unit on which a container accommodating a medical metal is detachably disposed and which is disposed to be movable in the through-hole, and a case unit which accommodates the lamp unit and the lifting unit and includes an outer case in which an outer hole corresponding to the through-hole is formed and an inner case which is disposed inside the outer case and in which the lamp unit or the lifting unit is disposed.

The lamp unit may include an excimer lamp in which the through-hole is formed along a central axis line thereof, and a cap in which an opening is formed at a position corresponding to the through-hole and which is disposed on one side surface of the excimer lamp.

At least one heat dissipation hole for dissipating heat from the excimer lamp may be formed in the cap.

The apparatus may further include a door unit which is disposed in the inner case to selectively close the opening of the cap.

The door unit may include a door motor disposed in the inner case, and a rotating piece which is fastened to a shaft of the door motor and rotated such that a free end thereof is moved between the opening of the cap and the outer hole of the outer case and which selectively closes the opening of the cap.

The lifting unit may include a lifting motor fixed to the inner case, a pinion gear which is disposed on a shaft of the lifting motor and rotates, and a shaft in which a rack gear engaged with the pinion gear is formed on an outer circumferential surface thereof and which is disposed to be movable in the through-hole.

The apparatus may further include a sensor unit configured to sense movement of the shaft.

The sensor unit may include a positioning bracket disposed on an outer circumferential surface of the shaft, and a pair of position sensing sensors which are spaced a predetermined interval from each other in the inner case and are in contact with the positioning bracket.

The apparatus may further include a fan which is disposed in the inner case to allow wind to flow in a direction toward the shaft.

The apparatus may further include an ozone removal unit which communicates with a hollow part of the shaft to remove ozone generated from the lamp unit, wherein the hollow part may be formed in the shaft.

The ozone removal unit may include a suction pump which is disposed in the inner case in order to allow air to flow from the hollow part of the shaft, a backflow preventer which is connected to the suction pump using a first pipe to prevent the air from flowing backward, an ozone filter connected to the backflow preventer using a second pipe, and a bracket which is connected to the ozone filter using a third pipe and accommodates one end of the shaft in which the other end thereof is disposed in the through-hole of the excimer lamp to be movable.

The apparatus may further include a door unit disposed in the inner case to selectively close an opening of a cap, a sensor unit configured to sense movement of the shaft, an ozone removal unit which communicates with the lifting unit to remove ozone generated from the lamp unit, and a substrate unit which is disposed on an inner side surface of the outer case or disposed in the inner case in order to control the door unit, the lifting unit, the sensor unit, or the ozone removal unit.

The substrate unit may stop driving of the lamp unit when the door unit is sensed to be opened or the shaft is sensed to be moved upward.

The substrate unit may drive the ozone removal unit from a preset time before a power source of the lamp unit is turned on to a time at which the preset time has elapsed after the power source of the lamp unit is turned off.

A slot into which an integrated circuit (IC) card is inserted may be formed in the outer case, a terminal into which the IC card inserted through the slot is mounted may be mounted on the substrate unit, and the substrate unit may control the lamp unit to be driven only when the IC card is inserted into the terminal.

Advantageous Effects

An apparatus according to the present invention includes a lamp unit for irradiating in all directions of a container accommodating a medical metal with ultraviolet rays, a lifting unit for mounting the container in the lamp unit having such a structure, and a fan for cooling a shaft of the lifting unit, thereby rapidly and effectively realizing modification of the surface of the medical metal.

In addition, an apparatus according to the present invention includes an ozone removal unit for removing ozone generated from the lamp unit and a substrate unit for controlling the apparatus, thereby achieving stable use of the apparatus.

[Modes of the Invention]

Hereinafter, exemplary embodiments of the present invention will be described in detail with reference to the accompanying drawings.

Unless otherwise defined, all terms in this specification have the same general meaning as terms understood by those skilled in the art, and if the terms used herein conflict with the general meaning of the terms, the terms used in this specification shall comply with the definitions used herein.

However, the invention to be described below is not intended to limit the scope of the present invention but to describe embodiments of the present invention, and the same reference numerals refer to the same components throughout this specification.

Figure 1:
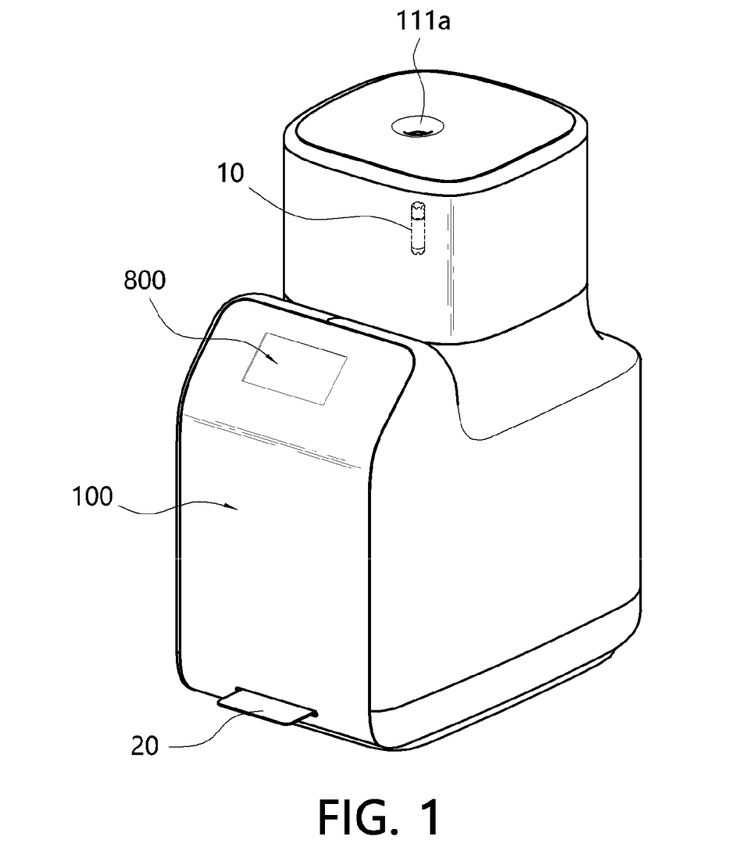
FIG. 1 is a perspective view of an apparatus for treating a surface of a medical metal according to an embodiment of the present invention.
Figure 2:
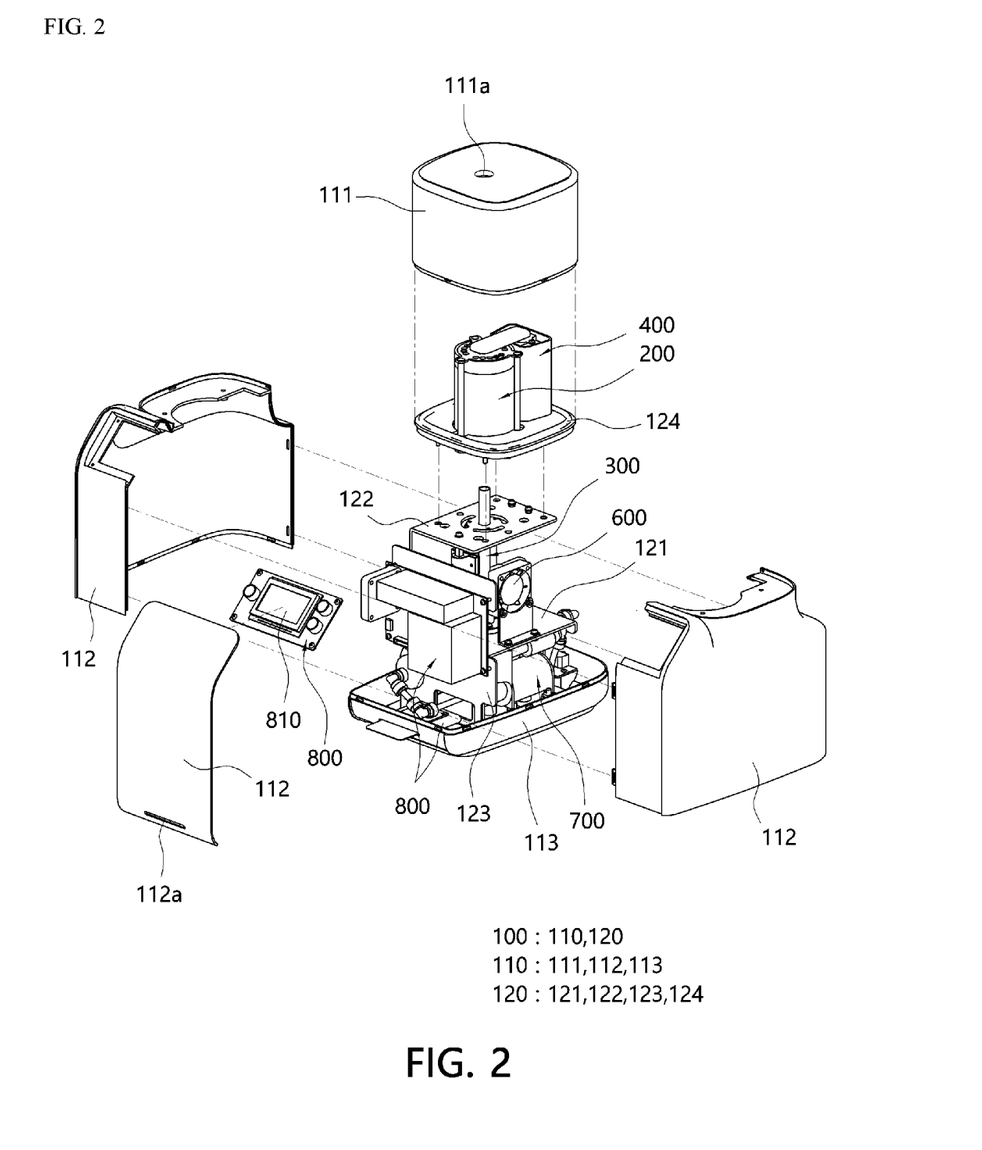
FIG. 2 is an exploded perspective view of an outer case, a lamp unit, and a door unit in FIG. 1.
Figure 3:
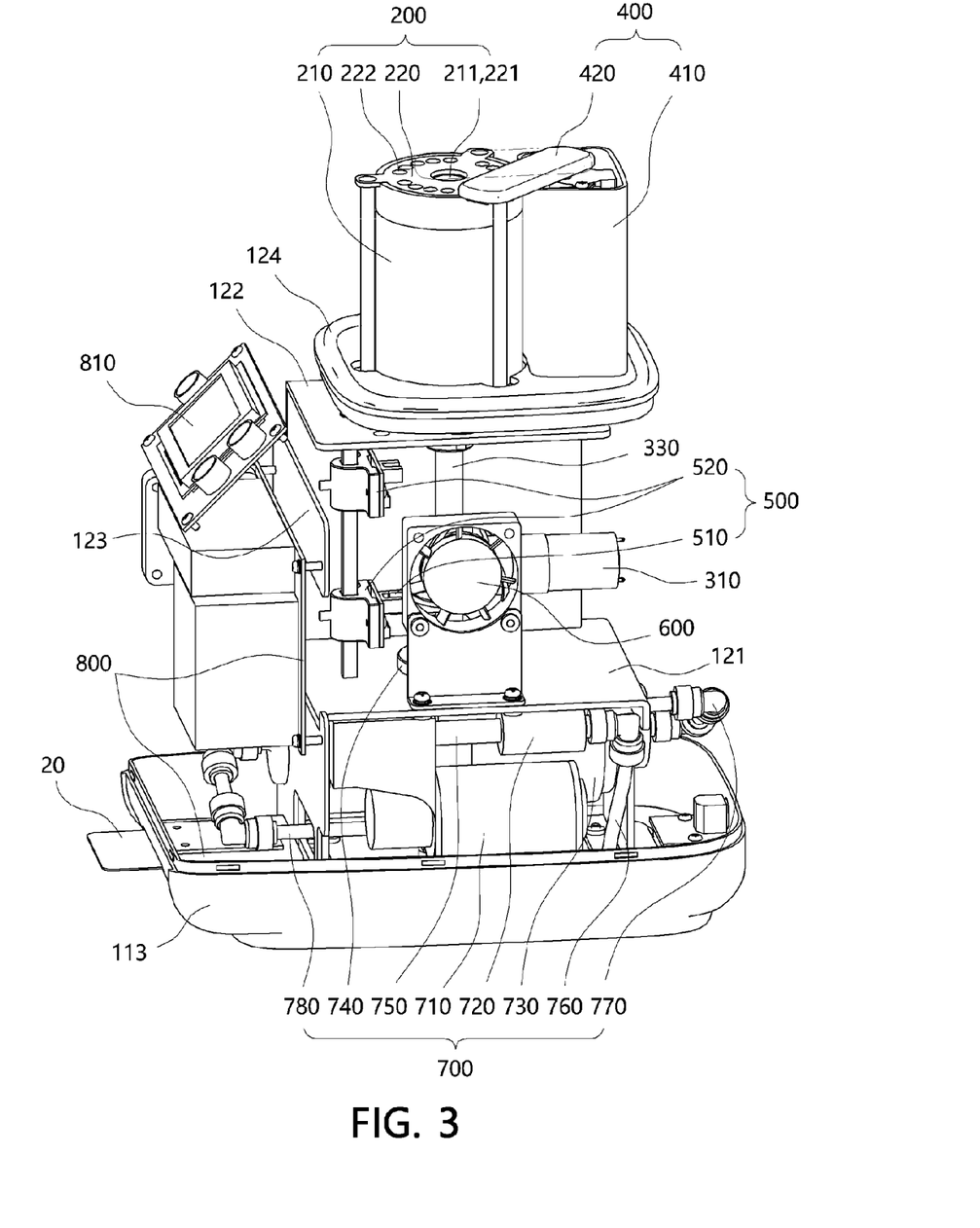
FIG. 3 is a perspective view of the apparatus for treating a surface of a medical metal of FIG. 1 from which the outer case is removed.
Figure 4:
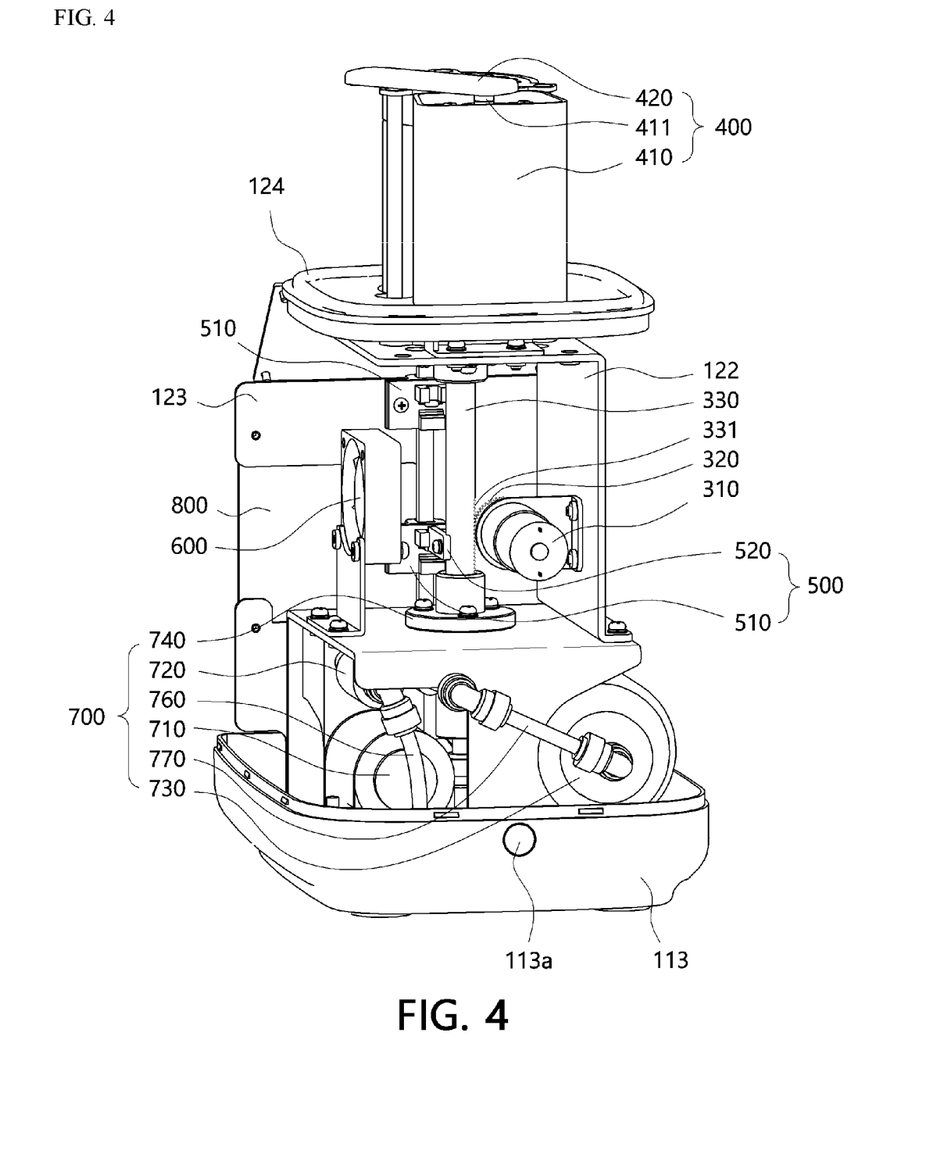
FIG. 4 is a view of FIG. 3 when viewed at another angle.
Figure 5:
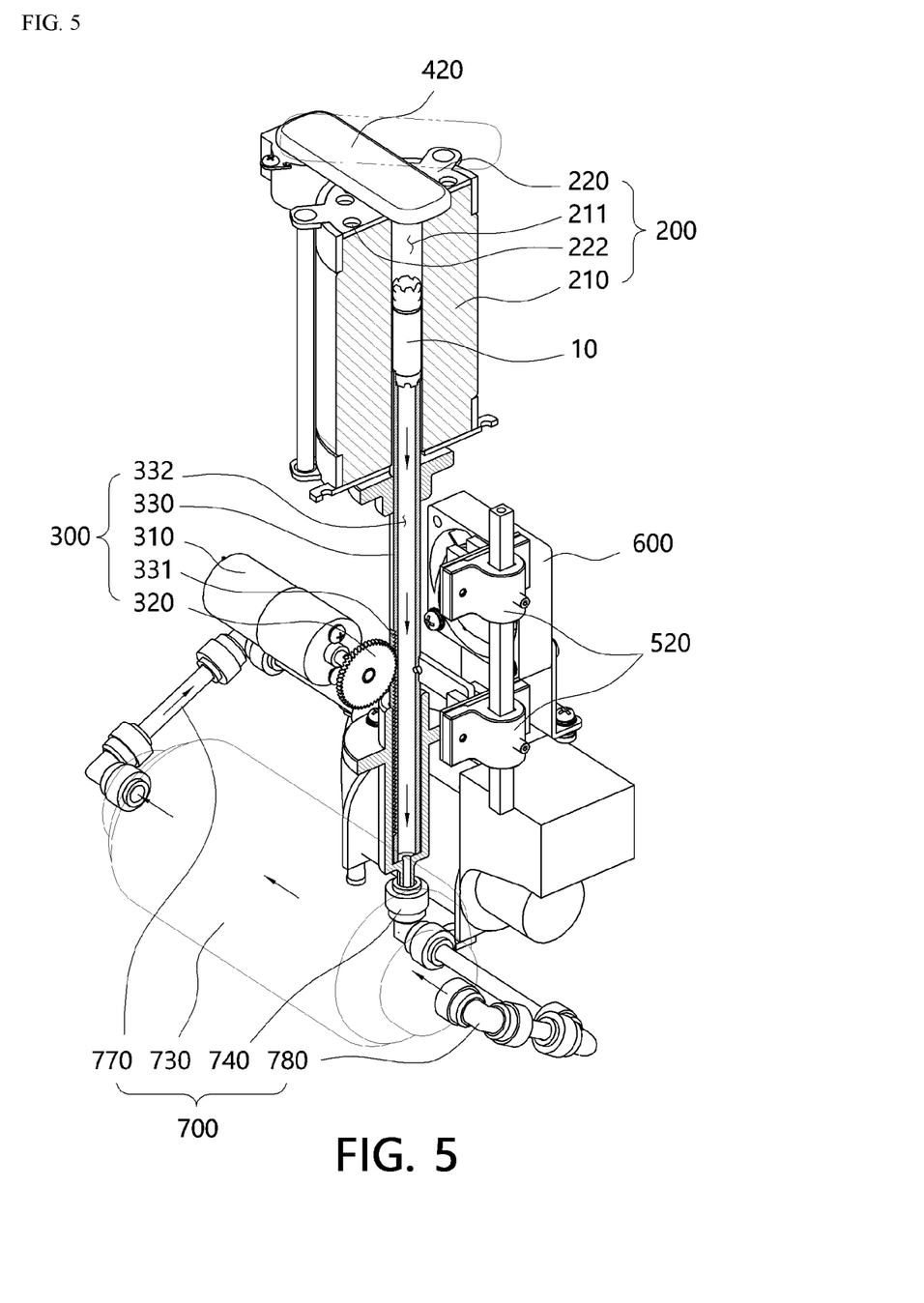
FIG. 5 is a partial cut away cross-sectional view of the apparatus for treating a surface of a medical metal according to the embodiment of the present invention.

FIG. 1 is a perspective view of an apparatus for treating a surface of a medical metal according to an embodiment of the present invention, FIG. 2 is an exploded perspective view of an outer case, a lamp unit, and a door unit in FIG. 1, FIG. 3 is a perspective view of the apparatus for treating a surface of a medical metal of FIG. 1 from which the outer case is removed, FIG. 4 is a view of FIG. 3 when viewed at another angle, and FIG. 5 is a partial cut away cross-sectional view of the apparatus for treating a surface of a medical metal according to the embodiment of the present invention.

Referring to FIGS. 1 to 5, the apparatus for treating a surface of a medical metal according to the embodiment of the present invention may include a case unit 100, a lamp unit 200, and a lifting unit 300, and further include a door unit 400, a sensor unit 500, a fan 600, an ozone removal unit 700, or a substrate unit 800.

Here, the medical metal may include any type of metal that may be implanted in a human body and may be any type of a medical part. For example, a material of the medical metal may be titanium or a titanium alloy and may be an implant fixture which is implanted in an alveolar bone.

The case unit 100 may include an outer case 110, which accommodates the lamp unit 200 and the lifting unit 300 to be described below and in which an outer hole 111a corresponding to a through-hole 211 of the lamp unit 200 to be described below is formed, and an inner case 120 which is disposed inside the outer case 110 and in which the lamp unit 200 or the lifting unit 300 to be described below is disposed.

The outer case 110 may form an exterior of the apparatus for treating a surface of a medical metal according to the embodiment of the present invention and may be divided into an upper case 111, a side case 112, and a lower case 113, but the present invention is not limited thereto.

Further, the outer hole 111a may be formed in an upper surface of the upper case 111, but the present invention is not limited thereto, and the outer hole 111a may be formed at a position in a direction in which the through-hole 211 of the lamp unit 200 is disposed.

Further, a terminal unit 113a to which a power unit for receiving external power may be connected may be disposed in the lower case 113, and the terminal unit 113a may supply power to a door motor 410, a lifting motor 310, the fan 600, or the substrate unit 800 to be described below.

Further, a slot 112a into which an integrated circuit (IC) card 20 is able to be implanted may be formed in the outer case 110. For example, the slot 112a may be formed in the side case 112 and/or the lower case 113.

The inner case 120 may be disposed inside the outer case 110 in order to arrange components to be described below.

For example, as illustrated in the drawings, the inner case 120 may include a first inner case 121 mounted on the lower case 113, and the ozone removal unit 700 to be described below may be disposed between the lower case 113 and the first inner case 121.

Further, a second inner case 122 may be disposed above the first inner case 121, and the lifting unit 300, the sensor unit 500, and the fan 600 to be described below may be disposed between the first inner case 121 and the second inner case 122.

Further, at least one third inner case 123 may be disposed on side surfaces of the first inner case 121 and the second inner case 122, and the substrate unit 800 to be described below may be disposed on the third inner case 123.

Further, a fourth inner case 124 that partitions an inner space of the outer case 110 may be provided such that the lamp unit 200 and the door unit 400 to be described below are disposed above the second inner case 122 and the remaining components are disposed below the second inner case 122.

Further, the first inner case 121 to the fourth inner case 124 may be integrally formed according to a shape of the outer case 110 or an arrangement of the internal components.

The lamp unit 200 may have the through-hole 211 formed therein and may irradiate the through-hole 211 with ultraviolet (UV) rays, thereby irradiating all directions of the container 10 accommodating the medical metal with UV rays.

Specifically, the lamp unit 200 may include an excimer lamp 210 in which the through-hole 211 is formed along a central axis line thereof, and a cap 220 in which an opening 221 is formed at a position corresponding to the through-hole 211 and which is disposed on one side surface of the excimer lamp 210.

Here, an inner circumferential surface of the excimer lamp 210 may be provided in a vacuum state in which the container 10 has an inner side made of quartz and is filled with discharge gas, and a discharge electrode may be provided in the inner side of the excimer lamp 210.

Further, a halogen gas such as fluorine, chlorine, or the like, or a gas such as xenon, krypton, or the like may be provided as the discharge gas.

The discharge electrode may be provided in the form of a rod, a spring, a pipe, or a conductive tape. Further, the discharge electrode may be formed of one selected from among a conductive material having high electrical conductivity, such as aluminum, an aluminum alloy, duralumin, copper, or a copper alloy, a conductive coating solution, such as silver paste, indium tin oxide (ITO), or aluminum tin oxide (ATO), and alloy steel having high resilience such as stainless steel or the like.

In the excimer lamp 210, the discharge gas with which the inside of the container 10 is filled in the vacuum state is discharged by an electric force formed in the discharge electrode so that excimer molecules (molecules in an excited state) are formed. When the excimer molecules are transitioned to a ground state, the excimer lamp 210 emits UV rays having a predetermined wavelength.

The emitted UV rays may not be emitted to the outside but may be emitted only in a direction along the inner side of the container 10 formed of a quartz material.

Therefore, in the present invention, since the UV rays emitted from the excimer lamp 210 are emitted in all directions of the container 10 accommodating the medical metal, the surface of the medical metal may be effectively modified to be a hydrophilic surface and sterilization and cleaning may be simultaneously performed by decomposing or removing remaining organic materials.

In this case, the excimer lamp 210 may emit far UV rays, particularly, vacuum UV rays, in a UV-C range having a wavelength in a range of 100 to 200 nm in the inside of the container 10 in the vacuum state. Such vacuum UV rays are emitted in a large amount in the vacuum state so that an amount of light is large and high energy of a short wavelength may be achieved, and thus the surface of the medical metal may be rapidly modified in a short time.

Alternatively, the excimer lamp 210 may emit far UV rays in a UV-C range having a wavelength in a range of 200 to 280 nm. Such far UV rays change outer electrons of oxygen molecules which are present inside and outside the container 10 to an excited state through an energy impact exceeding binding energy and change the oxygen molecules to ozone which is a reactive generator.

Accordingly, carbon atoms deposited on the surface of the medical metal are bonded to the ozone and separated from the surface, and thus the surface of the medical metal may be changed from hydrophilicity in a low energy state to hydrophilicity in a high energy state.

Meanwhile, the present invention may include a technical idea capable of processing the ozone generated by the lamp unit 200 because the ozone is harmful to the human body, which will be described in detail together with the ozone removal unit 700 to be described below.

The cap 220 may be disposed on an upper surface of the excimer lamp 210 and may be fastened to the inner case 120, for example, the second inner case 122 or the fourth inner case 124, in the same manner as bolt fastening to firmly fix the excimer lamp 210.

Further, the opening 221 of the cap 220 may be formed to be coaxial with the through-hole 211 of the excimer lamp 210 and the outer hole 111a of the upper case 111.

In addition, at least one heat dissipation hole 222 for dissipating heat of the excimer lamp 210 may be formed in the cap 220, thereby lowering a temperature of the medical metal.

As described above, the present invention may further include the door unit 400, and the door unit 400 may be disposed in the inner case 120 to selectively close the opening 221 of the cap 220.

The door unit 400 may close the through-hole 211 and the opening 221 to prevent the inflow of external foreign substances and prevent the release of the heat and ozone generated by the lamp unit 200.

Specifically, the door unit 400 may include the door motor 410 disposed in the inner case 120, and a rotating piece 420 which is fastened to a shaft 411 of the door motor 410 and rotated such that a free end thereof is moved between the opening 221 of the cap 220 and the outer hole 111a of the outer case 110 and which selectively closes the opening 221 of the cap 220.

Further, the door motor 410 may be fixed onto the fourth inner case 124. The cap 220 selectively closing the opening 221 may mean that the opening 221 of the cap 220 may be sealed by the control of the substrate unit 800 to be described below or by the manipulation of a control panel 810 by a user.

The container 10 accommodating the medical metal may be detachably disposed in the lifting unit 300, and the lifting unit 300 may be disposed to be movable in the through-hole 211.

Specifically, the lifting unit 300 may include the lifting motor 310 fixed to the inner case 120, a pinion gear 320 which is disposed on a shaft 330 of the lifting motor 310 and rotates, and the shaft 330 in which a rack gear 331 engaged with the pinion gear 320 is formed on an outer circumferential surface thereof and which is disposed to be movable in the through-hole 211.

Further, the lifting motor 310 may be driven by the control of the substrate unit 800 to be described below or by the manipulation of the control panel 810 by the user. For example, the lifting motor 310 may be fastened to a side surface of the second inner case 122 with a bolt and fixed.

Further, the container 10 accommodating the medical metal may be detachably disposed on one side of the shaft 330, the one side of the shaft 330 may be moved along the through-hole 211 of the lamp unit 200, and the other side of the shaft 330 may be moved along an inner side of a bracket 740 to be described below.

In addition, the shaft 330 may have a hollow part 332, and the hollow part 332 may communicate with the ozone removal unit 700 to be described below and the ozone may be removed.

As described above, the present invention may further include the sensor unit 500, and the sensor unit 500 may sense movement of the shaft 330.

Specifically, the sensor unit 500 may include a positioning bracket 510 disposed on an outer circumferential surface of the shaft 330, and a pair of position sensing sensors 520 which are spaced a predetermined interval from each other in the inner case 120 and are in contact with the positioning bracket 510.

A position of the shaft 330 sensed by the sensor unit 500 may be transmitted to the substrate unit 800 to be described below, and the substrate unit 800 to be described below may control the door unit 400 and/or the fan 600 and the ozone removal unit 700 to be described below according to the position information.

As described above, the present invention may further include the fan 600, and the fan 600 may be disposed in the inner case 120 to allow wind to flow in a direction toward the shaft 330.

For example, the fan 600 may be disposed in the second inner case 122.

Further, the fan 600 may be disposed to face the lifting motor 310 with the shaft 330 interposed therebetween, thereby effectively cooling the shaft 330 and rapidly cooling the medical metal.

Further, the fan 600 may be controlled to be driven by the substrate unit 800 to be described below. For example, the substrate unit 800 may drive the fan 600 from a time at which a preset time has elapsed after a power source of the lamp unit 200 is turned on to a time at which the preset time has elapsed after the power source of the lamp unit 200 is turned off.

As described above, the present invention may further include the ozone removal unit 700, and the ozone removal unit 700 may communicate with the lifting unit 300 to remove the ozone generated from the lamp unit 200.

Specifically, the ozone removal unit 700 may include a suction pump 710, a backflow preventer 720, an ozone filter 730, and the bracket 740. The above components may communicate with each other using a first pipe 750, a second pipe 770, and a third pipe 780.

The suction pump 710 may be disposed in the inner case 120 in order to allow air to flow from the hollow part of the shaft 330. For example, the suction pump 710 may be disposed on the lower case 113.

The backflow preventer 720 may be connected to the suction pump 710 using the first pipe 750 to prevent the air from flowing backward, and a discharge pipe 760 may be connected to the backflow preventer 720 to discharge the air purified by the ozone filter 730 to be described below to the discharge pipe 760.

For example, the discharge pipe 760 may be disposed to face a bottom surface of the lower case 113, and at least one discharge hole (not illustrated) may be formed on the bottom surface of the lower case 113.

The ozone filter 730 may be connected to the backflow preventer 720 using the second pipe 770 and may remove the ozone from the air containing the ozone introduced from the third pipe 780 to be described below.

The bracket 740 may be connected to the ozone filter 730 using the third pipe 780 and may accommodate the other end of the shaft 330 in which one end thereof is disposed in the through-hole 211 of the excimer lamp 210 to be movable.

For example, a first hole for accommodating the shaft 330 to be movable, and a second hole, which is formed to have a diameter smaller than that of the first hole and communicates with the first hole and the third pipe 780, may be formed inside the bracket 740.

That is, a level difference between the first hole and the second hole may finally cause a step in which the shaft 330 may be mounted.

That is, by driving the suction pump 710, the air containing the ozone which is present in the through-hole 211 of the excimer lamp 210 may be introduced into the ozone filter 730 through the hollow part 332 of the shaft 330 to remove the ozone and may be discharged from the discharge pipe 760 of the backflow preventer 720 toward the lower case 113.

Such an air flow may not only remove the ozone but also cool the through-hole 211 of the excimer lamp 210 and the hollow part 332 of the shaft 330.

As described above, the present invention may further include the substrate unit 800, and the substrate unit 800 may be disposed on an inner side surface of the outer case 110 or be disposed in the inner case 120 in order to control the door unit 400, the lifting unit 300, the sensing sensor unit 500, or the ozone removal unit 700.

Further, the substrate unit 800 may be electrically connected to the control panel 810 disposed on an outer side of the outer case 110.

Further, the control panel 810 may include a display for displaying a use state and the like and may be implemented as a touch panel.

Further, the substrate unit 800 may stop the driving of the lamp unit 200 when the door unit 400 is sensed to be opened or the shaft 330 is sensed to be moved upward and thus may prevent the ozone that can be generated from the lamp unit 200 from being discharged to the outside.

Further, the substrate unit 800 may drive the ozone removal unit 700 from a preset time before the power source of the lamp unit 200 is turned on to a time at which the preset time has elapsed after the power source of the lamp unit 200 is turned off to effectively remove the ozone generated from the lamp unit 200.

Further, a terminal into which the IC card 20 inserted through the slot 112a is mounted may be mounted on the substrate unit 800, and the substrate unit 800 may allow the lamp unit 200 to be driven only when the IC card 20 is inserted into the terminal, thereby further improving operational safety.

Further, the substrate unit 800 may determine whether the lamp unit 200 is driven a number of times which is preset in the individual IC card 20, and when it is determined that the lamp unit 200 is driven the preset number of times, the substrate unit 800 may stop the driving of the lamp unit 200.

In summary, the present invention may include the lamp unit 200 for irradiating in all directions of the container 10 accommodating the medical metal with UV rays, the lifting unit 300 for mounting the container 10 on the lamp unit 200 having such a structure, and the fan 600 for cooling the shaft 330 of the lifting unit 300, thereby rapidly and effectively realizing modification of the surface of the medical metal.

Further, the present invention may include the ozone removal unit 700 for removing the ozone generated from the lamp unit 200 and the substrate unit 800 for controlling the apparatus, thereby achieving stable use of the apparatus.

While embodiments of the present invention have been described above, these are only examples. It may be understood by those skilled in the art that various changes and modifications can be made without departing from the technical spirit of the present invention. Therefore, the technical scope of the present invention should not be limited to the contents described in the embodiments, but should be defined by the appended claims and encompasses equivalents that fall within the scope of the appended claims.

The invention claimed is:

1. An apparatus for treating a surface of a medical metal, the apparatus comprising:
 a lamp unit in which a through-hole is formed and which irradiates the through-hole with ultraviolet rays;
 a lifting unit on which a container accommodating a medical metal is detachably disposed and which is disposed to be movable in the through-hole; and
 a case unit which accommodates the lamp unit and the lifting unit and includes an outer case in which an outer hole corresponding to the through-hole is formed and an inner case which is disposed inside the outer case and in which the lamp unit or the lifting unit is disposed,
 wherein the lamp unit includes:
 an excimer lamp in which the through-hole is formed along a central axis line thereof; and
 a cap in which an opening is formed at a position corresponding to the through-hole and which is disposed on one side surface of the excimer lamp,
 wherein at least one heat dissipation hole for dissipating heat from the excimer lamp is formed in the cap, and
 wherein the lifting unit includes:
 a lifting motor fixed to the inner case;
 a pinion gear which is disposed on a shaft of the lifting motor and rotates; and
 a shaft in which a rack gear engaged with the pinion gear is formed on an outer circumferential surface thereof and which is disposed to be movable in the through-hole.

2. The apparatus of claim 1, further comprising a door unit which is disposed in the inner case to selectively close the opening of the cap.

3. The apparatus of claim 2, wherein the door unit includes:
 a door motor disposed in the inner case; and
 a rotating piece which is fastened to a shaft of the door motor and rotated such that a free end thereof is moved between the opening of the cap and the outer hole of the outer case and which selectively closes the opening of the cap.

4. The apparatus of claim 1, further comprising a sensor unit configured to sense movement of the shaft.

5. The apparatus of claim 4, wherein the sensor unit includes:
 a positioning bracket disposed on the outer circumferential surface of the shaft; and
 a pair of position sensing sensors which are spaced a predetermined interval from each other in the inner case and are in contact with the positioning bracket.

6. The apparatus of claim 1, further comprising a fan which is disposed in the inner case to allow wind to flow in a direction toward the shaft.

7. The apparatus of claim 1, further comprising an ozone removal unit which communicates with a hollow part of the shaft to remove ozone generated from the lamp unit,
 wherein the hollow part is formed in the shaft.

8. The apparatus of claim 7, wherein the ozone removal unit includes:
 a suction pump which is disposed in the inner case in order to allow air to flow from the hollow part of the shaft;
 a backflow preventer which is connected to the suction pump using a first pipe to prevent the air from flowing backward;
 an ozone filter connected to the backflow preventer using a second pipe; and
 a bracket which is connected to the ozone filter using a third pipe and accommodates one end of the shaft in which the other end thereof is disposed in the through-hole of the excimer lamp to be movable.

9. The apparatus of claim 1, further comprising:
 a door unit disposed in the inner case to selectively close an opening of a cap;
 a sensor unit configured to sense movement of the shaft;
 an ozone removal unit which communicates with the lifting unit to remove ozone generated from the lamp unit; and
 a substrate unit which is disposed on an inner side surface of the outer case or disposed in the inner case in order to control the door unit, the lifting unit, the sensor unit, or the ozone removal unit.

10. The apparatus of claim 9, wherein the substrate unit stops driving of the lamp unit when the door unit is sensed to be opened or the shaft is sensed to be moved upward.

11. The apparatus of claim 9, wherein the substrate unit drives the ozone removal unit from a preset time before a power source of the lamp unit is turned on to a time at which the preset time has elapsed after the power source of the lamp unit is turned off.

12. The apparatus of claim 9, wherein:
 a slot into which an integrated circuit (IC) card is inserted is formed in the outer case;
 a terminal into which the IC card inserted through the slot is mounted is mounted on the substrate unit; and
 the substrate unit controls the lamp unit to be driven only when the IC card is inserted into the terminal.

\* \* \* \* \*